(12) United States Patent
Zhang et al.

(10) Patent No.: US 8,262,728 B2
(45) Date of Patent: Sep. 11, 2012

(54) INTRA-OCULAR DEVICE WITH MULTIPLE FOCUSING POWERS/OPTICS

(75) Inventors: Xiaoxiao Zhang, Fort Worth, TX (US);
Richard J. Mackool, Astoria, NY (US);
Xin Hong, Arlington, TX (US); Michael A. Southard, Arlington, TX (US)

(73) Assignee: Novartis, AG, Basel (CH)

(*) Notice: Subject to any disclaimer, the term of this patent is extended or adjusted under 35 U.S.C. 154(b) by 228 days.

(21) Appl. No.: 12/776,807

(22) Filed: May 10, 2010

(65) Prior Publication Data

US 2010/0286771 A1    Nov. 11, 2010

Related U.S. Application Data

(63) Continuation of application No. 11/350,437, filed on Feb. 9, 2006, now abandoned.

(51) Int. Cl.
*A61F 2/16* (2006.01)

(52) U.S. Cl. ...................... 623/6.25; 623/6.27

(58) Field of Classification Search ............... 623/6.17, 623/6.23, 6.24, 6.25, 6.27, 6.28, 6.3, 6.31
See application file for complete search history.

(56) References Cited

U.S. PATENT DOCUMENTS

| | | |
|---|---|---|
| 4,888,012 A | 12/1989 | Horn et al. |
| 5,112,351 A * | 5/1992 | Christie et al. ............... 623/6.28 |
| 5,217,489 A | 6/1993 | Van Noy et al. |
| 5,699,142 A | 12/1997 | Lee et al. |
| 5,895,422 A | 4/1999 | Hauber |
| 6,432,246 B1 | 8/2002 | Blake |
| 6,596,026 B1 | 7/2003 | Gross et al. |
| 6,599,317 B1 | 7/2003 | Weinschenk, III et al. |
| 6,638,305 B2 | 10/2003 | Laguette |
| 6,695,881 B2 | 2/2004 | Peng et al. |
| 6,969,403 B2 | 11/2005 | Peng et al. |
| 2003/0014107 A1 | 1/2003 | Reynard |
| 2004/0252274 A1 | 12/2004 | Morris et al. |
| 2005/0209692 A1 | 9/2005 | Zhang |
| 2006/0055883 A1 | 3/2006 | Morris et al. |

FOREIGN PATENT DOCUMENTS

WO    2006/023404 A2    3/2006

OTHER PUBLICATIONS

European Search Report for Application No. 07101409.6, Publication No. EP 1818023, Published Aug. 15, 2007, dated May 16, 2007, 2 pages.

* cited by examiner

*Primary Examiner* — David Isabella
*Assistant Examiner* — Randy Shay
(74) *Attorney, Agent, or Firm* — Jonathan E. Prejean

(57) ABSTRACT

An intraocular lens device that includes an intraocular lens optics that provides at least two powers of magnification one being near vision power and the other being distance vision power. The lens optics has surface modulations that are responsible for providing the near vision power. The zone structure provides an add power of over 6 diopters. The add power indicative of an extent that the near vision focusing power is greater than the distance vision focusing power.

9 Claims, 3 Drawing Sheets

Nasal retina (degrees from fixation)

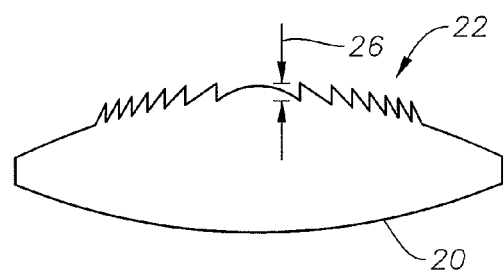
Fig. 6
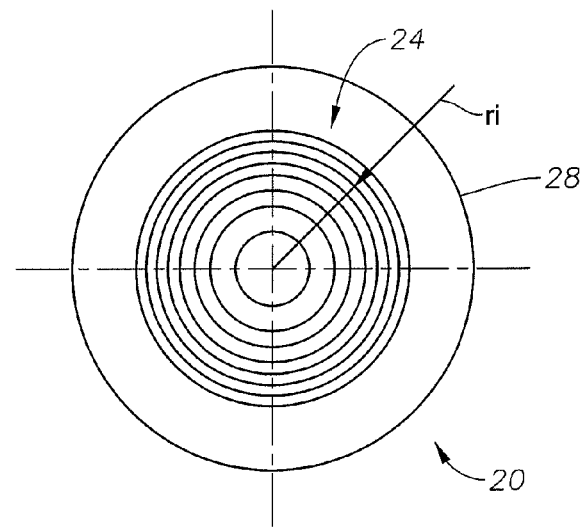
Fig. 7
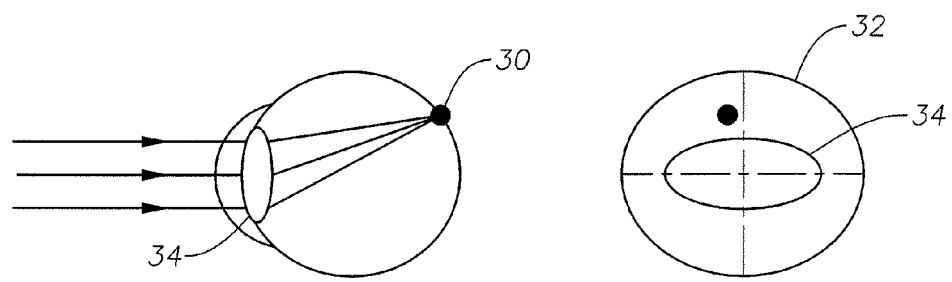
Fig. 8
Fig. 9

INTRA-OCULAR DEVICE WITH MULTIPLE FOCUSING POWERS/OPTICS

This application is a continuation of and claims priority to U.S. application Ser. No. 11/350,437 filed on Feb. 9, 2006 now abandoned.

BACKGROUND OF THE INVENTION

1. Field of the Invention

The invention relates to a vision aid for the amblyopic population, inclusive of patients with age-related macular degeneration (AMD) or other low vision conditions. The vision aid is an intra-ocular lens (IOL) device that has multiple focusing powers or optics.

2. Discussion of Related Art

Age-related macular degeneration (AMD) patients usually have impaired central visual fields and often rely heavily on peripheral vision for daily tasks. Peripheral retina has low receptors (cons and rods) densities, which lead to their poor resolution ability. Low vision patients, such as the amblyopic population, also have poor retina resolutions. For these patients, the bottle neck of visual resolution is at retina resolution. Improving optical imagery in details does not solve the problem of poor visual resolution.

AMD patients often have compromised fovea. However, there are still functional retina receptors surrounding the compromised receptors. These functional retina receptors are often peripherally located and have larger spacing between each other. The increase spacing leads to decreased image resolution ability of the retina. For example, at 3 degrees nasal retina, the visual acuity is reduced to 0.4 compared to the 1.0 visual acuity at 0 degrees; at 5 degrees nasal retina, the visual acuity is reduced to 0.34 compared to the 1.0 visual acuity at 0 degrees (Millodot, 1966).

There are three basic types of vision aids available conventionally either individually or in combination.

The first type is a single telescope as the visual aid. The telescopes are often mounted on the spectacles, which are heavy and are not appealing cosmetically. Implanted telescopes often require very large incisions during surgery to implant. The main disadvantage of using a telescope system alone is the resultant narrow visual field of view and overall poor image quality, which could cause a safety concern during motion.

The second type of vision aid is a prism. The prism is to realign the line of sight to the peripheral retina. This application needs to overcome a binocular fusion problem in order to avoid double imagery. Also, the prism does not magnify the retinal images. Therefore, the problem of low visual resolution due to the larger peripheral retina receptor spacing is not resolved.

The third type of vision aid is a magnifying glass, sometimes combined with a prism. This visual aid is often used as a desk mount device, which limits the application range for patients. The handheld version of this visual aid has vision instability and focus problems for patients with hand tremors.

Therefore, there are needs to 1) keep a larger visual field of view, 2) increase portability for application, 3) improve cosmetics, and 4) increase the quality of vision and the stability of the application.

FIG. 1 shows Peripheral Visual Acuity from Bennett and Rabbetts "Clinical Visual Optics" page 37, Butterworth, Boston, 1984.

It is known that the peripheral vision can still provide adequate resolution. The resolution, however, is progressively reduced (FIG. 1). As shown in FIG. 1, visual acuity is reduced to 0.5 at 2 degrees nasally, to 0.4 at 3 degrees nasally, to 0.34 at 5 degree nasally, relative to the 1.0 visual acuity at 0 degrees. Temporal, superior and inferior peripheral retinas are expected to have similar behavior at similar small degree off axis range. Accordingly, increasing or magnifying retina image size relative to the size associated with 14 inches reading distance could allow the peripheral retina to enable visual acuity comparable to that of central 0 degrees retina. In particular, the magnification could be 2 times for using 2 degrees peripheral retina, 2.5 times for using 3 degrees peripheral retina, or 3 times for using 5 degrees peripheral retina.

Bifocal and multifocal optics are well known in the ophthalmic optics field. Alcon's ReSTOR® lens optics is an example. However, existing ophthalmic bifocal or multifocal optics have much lower add power by design because they are obligated to suit different patient needs. The ReSTOR® lens has a 4 D IOL add power which is likely the highest add power known for commercially available products. Table 1 indicates that with a 4 D add power the magnification is only 1.2 times. That 1.2 times value is not likely to be adequate for AMD application according to the needs shown in FIG. 1. That is, 1.2 times magnification is only useful if the 0.5 degrees retina is not damaged by AMD.

SUMMARY OF THE INVENTION

One aspect of the invention pertains to a bifocal or multifocal IOL or system that provides at least two focusing powers or optics systems. While providing the distance power for normal wide visual field needs of AMD and other low vision patients, the IOL of the present invention enables such patients to focus reading materials at near distances by employing surface modulations in a zone structure, preferably modulations in a diffractive zone structure resembling a series of ring configurations of increasing diameter.

Such near distances lead to clear retina images that are magnified larger than 1.2 times of those normal reading retinal images associated with reading distance of about 14 inches. Preferably, the near distance power leads to clear retina images that are magnified to 2-3 times of the normal reading retinal images.

Reading needs of AMD patients can be met with the invention preferably by bringing the magnified and focused retinal images to the peripheral retinal receptors when patients position the normal reading text to be focused via the near distance power. The invention also provides the normal visual field of view needs that can not be provided by telescopic devices used for AMD and other low vision patients. This is achieved by making provisions to incorporate a distance focus power capability. In addition, the stable IOL position provides stable vision for patients with hand tremors.

BRIEF DESCRIPTION OF THE DRAWINGS

For a better understanding of the present invention, reference is made to the following description and accompanying drawings, while the scope of the invention is set forth in the appended claims.

FIG. 6 is a schematic elevation view of a diffractive multifocal lens with a sawtooth surface modulation in accordance with an embodiment of the invention.

FIG. 7 is a top plan view of the embodiment of FIG. 6, revealing a ring diffractive zone structure.

FIG. 8 is a schematic side view representation of the eye with an intraocular implant in accordance with an embodiment of the invention.

FIG. 9 is a schematic front view representation of the eye with the intraocular implant of FIG. 8.

DETAILED DESCRIPTION OF THE PREFERRED EMBODIMENT

The inventors of the present invention are aware of sight problems faced by patients with AMD or low vision and are aware that such patients use add powers in reading glasses to help improve their seeing ability.

Placing a strong add power in a reading glass will provide a bigger magnified image, but such gives fewer photons per receptor than would be the case if the same strong add power were placed in an intraocular lens. By placing the strong add power into the intraocular lens, such provides better contrast sensitivity for patients with AMD or low vision disorders than would be the case if the strong add power is in the reading glass instead—reason for this difference is due to optics.

By placing the strong add power into the intraocular lens, such provides a greater photon per receptor concentration as compared to strong add power in the reading glass. The inventors have determined that the add power of the lens implant be greater than the current conventional level of 4 diopters on the lens itself—the effect on the patient's vision is about 2.75 diopters. Preferably, the add powers should be increased to any stronger add power that would effect the patient's vision by as much as 5, 7.5 and 10 diopters and potentially higher.

There are at least the following three patient populations that can potentially benefit from the invention.

Population 1: IOL patients that developed AMD

Population 2: Non-cataract presbyopic patients that developed AMD.

Population 3: Non-cataract Non-presbyopic patients that developed AMD or Low vision patients (amblyopic population).

Figure 1:
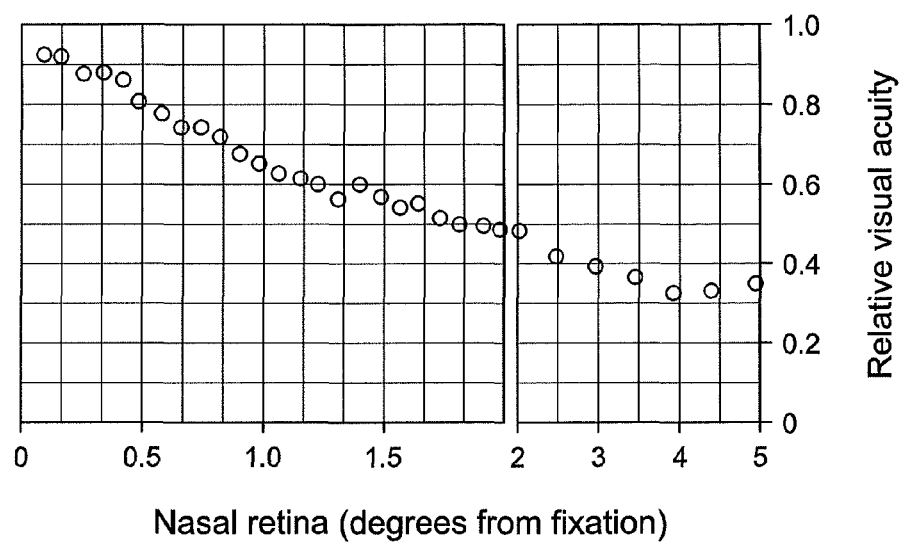
FIG. 1 is a conventional graphical representation of visual acuity as a function of eccentricity in the nasal retina.
Figure 2:
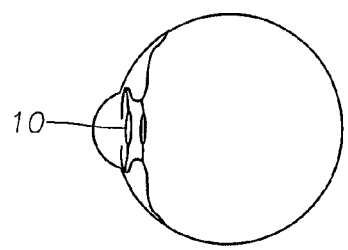
FIG. 2 is a schematic representation of a bifocal/multifocal on a sulcus fixed IOL carrier in accordance with an embodiment of this invention.

Device approach for Population 1: Use a bifocal/multifocal IOL10 on a sulcus fixed IOL carrier as shown in FIG. 2. The distant power is plano or near plano for the patient's distance vision and normal visual field size. The near add power will allow the patient to see close enough (e.g. 6-7 inches) so that the retinal image size of the normal reading text is resolvable by the good retinal receptor array. As a placement alternative, this bifocal/multifocal can also be on an anterior chamber IOL carrier and put into the anterior chamber of the eye.

Figure 3:
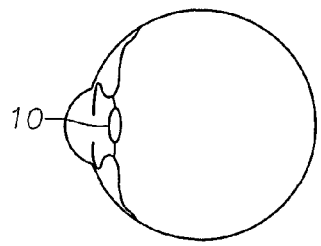
FIG. 3 is a schematic representation of a bifocal/multifocal IOL in a capsular bag accordance with a further embodiment of the invention.

Device approach for Population 2: Use a Bifocal/Multifocal IOL10 in a capsular bag as shown in FIG. 3. The distance vision power is selected for the patient's distance vision needs and normal visual field size. The near vision power will allow the patient to see close enough (e.g. 6-7 inches) so that the retinal image size of the normal reading text is resolvable by the good retinal receptor array.

Figure 4:
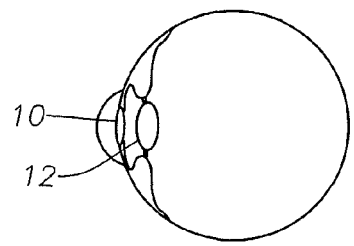
FIG. 4 is a schematic representation of a bifocal/multifocal IOL in an anterior chamber or sulcus, plus an IOL in a capsular bag, in accordance with another embodiment of the invention.

Device approach for Population 3: Use a bifocal/multifocal IOL10 in an anterior chamber or sulcus fixed IOL carrier plus an IOL12 in the capsular bag as shown in FIG. 4. The multilens multifocal system has at least one telescopic view system (e.g. IOL10) together with a non-telescopic view system (e.g., IOL12). The telescopic system provides magnified retina image for visual acuity improvement. The non-telescopic view system provides the normal visual field of view. In cases that the natural accommodation of the natural crystalline lens is to be preserved, a different embodiment can be used in which the natural crystalline lens will be kept to work with a bifocal/multifocal IOL in an anterior chamber or sulcus fixed IOL carrier. In such cases the magnified retinal images are provided via the higher add power of the bifocal/multifocal IOL.

Any other cross application of the three approaches to any of the three populations is anticipated by the inventors. Also, other forms of IOL lens carrier for the bifocal/multifocal IOL such as iris fixated IOL carriers, is envisioned. This visual aid device could also be used together with commercially available AMD drugs and/or contact lenses and refractive ablations. The drug will steady and stabilize the vision to help the device improve the patient vision and the surgery or device can help to improve the patient's vision.

In view of FIGS. 2-4, the present invention addresses the need to keep a larger visual field of view than that provided by the three basic types of vision aids available conventionally as previously discussed by using bifocal or multifocal optics. The present invention also addresses the needs for an increase in portability for application and for an improvement in cosmetics over such conventionally basic types and by implementing the optics inside the eye in a conventional minimally invasivce surgical procedure, unlike implanted telescopes.

The inventive bifocal or multifocal device or IOL provides at least two focusing powers. Patients' normal wide visual field needs are met by the distance power of the device. Patients' reading needs are met by allowing the patients to see focused images at a closer sight distance than the normal 14 inches for near distance. Image quality is also based on a focused image rather that a patient having to orient his/her head or eyes.

With first order optics estimation, the retina Image size magnification as a function of an IOL power can be found by using equation 1 below.

$$\beta = f_1 \times f_2 \div (f_1 \times f_1' - x_1 \times \Delta) \qquad \text{Equation (1)}$$

Where $\beta$ is the Image magnification of a optical system, $f_1$ is the object space focal length of the first optical lens of the system, $f_2$ is the object space focal length of the second optical lens of the system, $f_1'$ is the image space focal length of the first optical lens of the system, $x_1$ is the object distance from the object space focal point, $\Delta$ is the separation distance between the principal plane of the first lens and the principal plane of the second lens.

Assuming the first lens is the cornea and has a power of 43 diopters, the $\Delta$ is 4.3 mm, the refractive index in the image space is 1.336, the distance power of the IOL is about +18 Diopters. Decreasing the object vergence distance increases the IOL add power. Exemplary calculations using Equation (1) are tabulated in Table 1.

TABLE 1 retina Image size change as a function of the IOL power.

| Distance (mm) | Distance (in) | IOL near power | $\beta$ | Image size change relative to that of 14.3 inches | Note |
|---|---|---|---|---|---|
| −500 | −19.7 | 21.0 | 0.081 | 0.7 | |
| −444 | −17.5 | 21.3 | 0.092 | 0.8 | |
| −400 | −15.7 | 21.5 | 0.103 | 0.9 | |
| −364 | −14.3 | 21.8 | 0.114 | 1.0 | Jager chart testing distance |
| −333 | −13.1 | 22.0 | 0.126 | 1.1 | |

TABLE 1-continued retina Image size change as a function of the IOL power.

| Distance (mm) | Distance (in) | IOL near power | β | Image size change relative to that of 14.3 inches | Note |
|---|---|---|---|---|---|
| −308 | −12.1 | 22.3 | 0.137 | 1.2 | ReSTOR magnification |
| −286 | −11.2 | 22.5 | 0.149 | 1.3 | |
| −287 | −10.5 | 22.8 | 0.161 | 1.4 | |
| −250 | −9.8 | 23.0 | 0.173 | 1.5 | |
| −235 | −0.3 | 23.3 | 0.185 | 1.6 | |
| −222 | −8.7 | 23.5 | 0.197 | 1.7 | |
| −211 | −8.3 | 23.8 | 0.210 | 1.8 | |
| −200 | −7.9 | 24.0 | 0.222 | 1.9 | |
| −190 | −7.5 | 24.3 | 0.235 | 2.1 | see J1 text (Times New Roman N4 font) with 2 degree nasal retina |
| −182 | −7.2 | 24.5 | 0.247 | 2.2 | |
| −174 | −8.8 | 24.8 | 0.260 | 2.3 | |
| −167 | −8.8 | 25.0 | 0.273 | 2.4 | |
| −160 | −8.3 | 25.3 | 0.286 | 2.5 | See J1 text (Times New Roman N4 font) with 3 degree nasal retina |
| −154 | −6.1 | 25.5 | 0.299 | 2.8 | |
| −148 | −5.8 | 25.8 | 0.313 | 2.7 | |
| −143 | −5.6 | 26.0 | 0.26 | 2.9 | |
| −138 | −5.4 | 26.3 | 0.339 | 30. | see J1 text (Times New Roman N4 font) with 5 degree nasal retina |
| −133 | −5.2 | 26.5 | 0.353 | 3.1 | |
| −129 | −5.1 | 26.8 | 0.366 | 3.2 | |
| −125 | −4.9 | 27.0 | 0.379 | 3.3 | |

Figure 5:
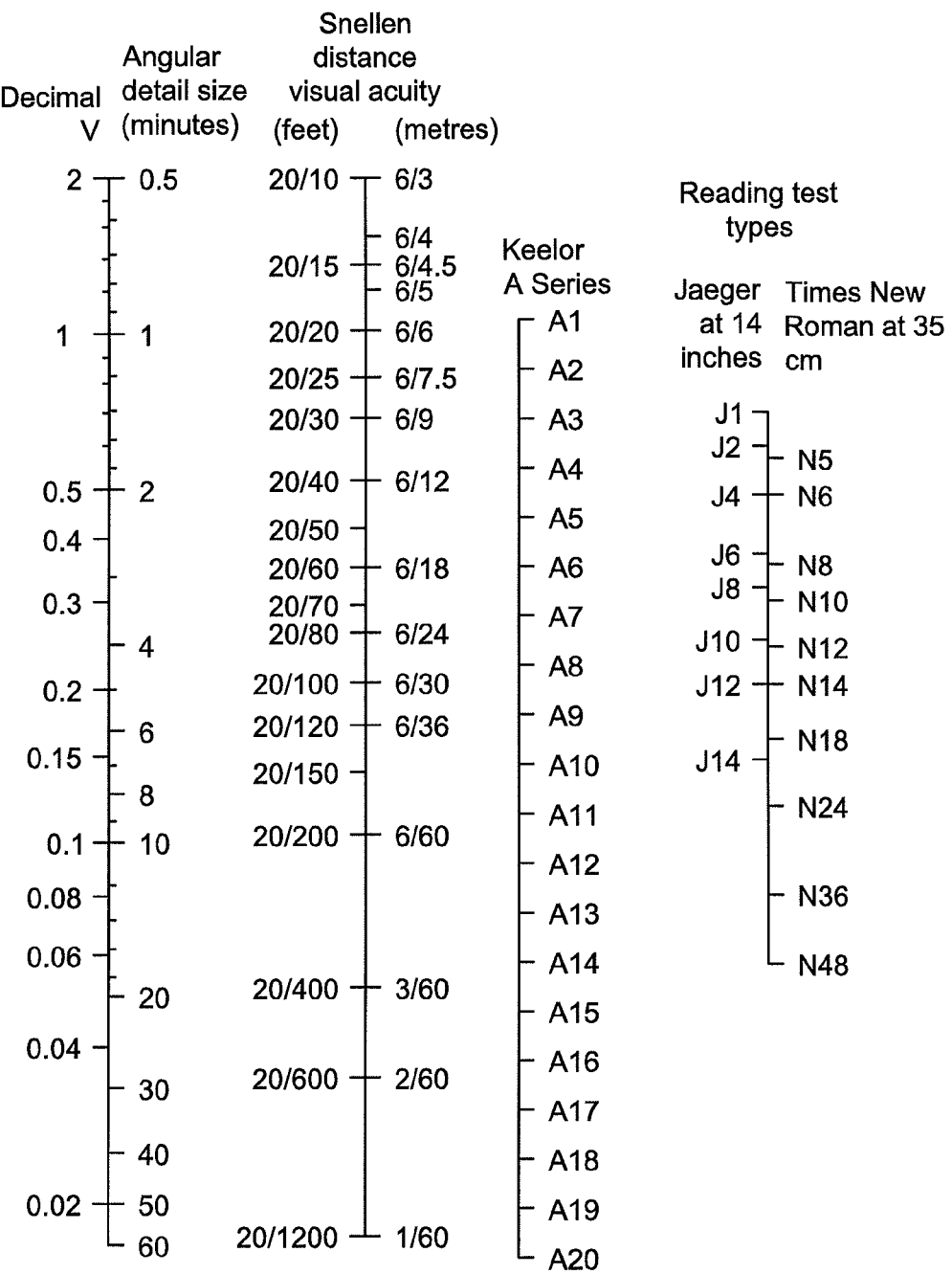
FIG. 5 is a conventional representation of different acuity scales depicting a relationship between them.

In the table note, the text font size estimation is based on FIG. 5.

Once the image size is magnified enough, the corresponding focus power or imaging capability will bring a focused clear image to the retina. Normal eye optics do not provide imaging capability for bringing a focused clear image to retina at such close distance except in very young children eyes.

While the accurate calculation could be done through ray tracing, the above approximation should illustrate the concept. With the present inventive device, AMD patients could have normal visual field of view during motion except with a central Scotoma. When they need to read text, reading ability is triggered by bringing the text close to get a clearly focused image. Times New Roman fonts of N4 or N5 are very small, and patients could read these texts at 8 to 5.5 inches with retina adjacent to fovea (depending on their Scotoma size).

Therefore, the invention modifies bifocal and multifocal optics to provide an "add" power >+6 diopters in the IOL plane. The preferred "add" power is >+6 to +8 diopters depending on reading distance needs, although any greater power, such as 9 diopters or 10 diopters, is envisioned. The "add" power is the difference between the near vision power and the distance vision power of the bifocal or multifocal IOL.

The construction of the bifocal/multifocal optics of the present invention is a variation of constructions available conventionally. Such conventional constructions provide a lesser difference between the near vision power and the distance vision power than 6 diopters. Some examples of conventional constructions include that of U.S. Pat. No. 5,217,489 that mentions that the near vision power is greater than the distance vision power by 2.0-5.0 diopters and whose contents are incorporated herein by reference with respect to its bifocal intraocular lens structure.

U.S. Pat. No. 4,888,012 discloses an accommodative lens that differs from the present invention in at least the following two aspects. First, the said accommodative lens is a lens that theoretically changes its power as the ciliary muscle compresses it, instead of a predetermined multifocal lens. Second, the accommodative lens only has a single focus instead of multiple foci simultaneously. Therefore, U.S. Pat. No. 4,888,012 does not disclose high add power values for multifocal lenses that have simultaneously multiple foci which the present invention refers to.

U.S. Pat. No. 6,432,246 B1 reveals a type of multifocal lens known as progressive multifocal lens. Such a lens achieves power variations across the lens optic by changing the surface radius of curvature. This is based on the principle of geometric optics instead of the diffractive optics principle. The progressive multifocal lens has to deliver light over a wide range of foci and thus reduces the available light energy for individual focus. Therefore, it is not as effective as the diffractive optics multifocal IOL in this regard. Therefore, U.S. Pat. No. 6,432,246 B1 does not disclose high add power values for multifocal lenses that rely on diffractive optics principle to generated distinct and highly efficient multiple foci, which the present invention refers to.

Other conventional constructions include those of U.S. Pat. No. 6,969,403 B2, U.S. Pat. No. 6,695,881 B2, and U.S. Published Patent Application No. US 2005/0209692 A1, each of which being incorporated herein by reference with respect to their structures of an intraocular lens and carrier of the same.

Given the objective of providing low vision patients the near reading ability as well as the normal field of view, light energy is preferred to be concentrated at well defined specific (i.e. distinct) foci such as distance focus and near focus, in some cases also including an intermediate focus. Diffractive multifocal lenses are more effective in this regard.

Diffractive multifocal lenses are often made with surface modulation to achieve light interference for focus creation. The add power of such lenses is related to the size of the concentric rings of the surface modulation structure. By way of example, a diffractive bifocal 20 can have a sawtooth shape surface modulation 22 as shown in FIG. 6. The ring structure 24 (also known as diffractive zone structure) is better illustrated by FIG. 7. This ring structure can be defined as a function of the add power needed by equation 2 below, $$r_i^2 = (2i+1)\lambda f \qquad \text{Equation (2)}$$

wherein $r_i$ denotes the radial distance of each diffractive zone in the ring pattern i denotes the zone number (i=0 denotes the central zone), λ denotes the design wavelength, f denotes an add power.

The sawtooth shape has a feature of step height 26 as shown in FIG. 6. The step height 26 at each zone boundary of the bifocal diffractive pattern can be defined by equation 3:

$$\text{Step height} = \frac{\lambda}{a(n_2 - n_1)} f_{apodize}. \qquad \text{Equation (3)}$$

wherein

λ denotes a design wavelength (e.g., 550 nm),

α denotes a parameter that can be adjusted to control diffraction efficiency associated with various orders, e.g., α can be selected to be 2, $n_2$ denotes the index of refraction of the optic, $n_1$ denotes the refractive index of a medium in which the lens is placed. In embodiments in which the surrounding medium is the aqueous humor having an index of refraction of 1.336, the refractive index of the optic ($n_2$) can be selected to be 1.55.

and $f_{apodize}$ represents a scaling function whose value decreases as a function of increasing radial distance from the intersection of the optical axis with the anterior surface of the lens.

By way of example, the scaling function $f_{apodize}$ can be defined by equation 4:

$$f_{apodize} = 1 - \left(\frac{r_i}{r_{out}}\right)^3. \qquad \text{Equation (4)}$$

wherein $r_i$ denotes the radial distance of the $i^{th}$ zone, $r_{out}$ denotes the outer radius of the last bifocal diffractive zone.

In embodiments in which the near focus light energy need is high, the $f_{apodize}$ scaling function can be assigned with other values. For example, $f_{apodize}$ can be a constant of 1.0.

The step heights 26 provided by the above equations are only examples, and other step heights can also be utilized.

The near vision focus power is provided by the diffraction zone structure 24, while the distance vision focus power is provided by the region 28 outside the diffraction zone structure 24 and by the diffraction zone structure 24. When there is an optimal intermediate focus need for the AMD or low vision patients, a trifocal-style multifocal lens can also be applied for as a low vision aid use with high add power values.

Refractive multifocal lenses such as disclosed in U.S. Pat. No. 5,217,489 can be changed upon higher add power and improved light energy concentration at distance focus and near focus, as anticipated by the inventors. The present invention has bifocal or multifocal lenses with distinct foci that is as diffractive and refractive as, although more diffractive and refractive than, that disclosed in U.S. Pat. No. 5,217,489, but not utilizing progressive multifocal lens in the manner of U.S. Pat. No. 6,432,246 B1.

Turning to FIGS. 9 and 10, a further embodiment is shown illustrating the concept of deflecting an image 30 to functional retina 32 and thereby avoid scotoma in the visual field. The intraocular lens 34 is configured to effect the deflection as shown, which is helpful for low vision patients such as those with AMD and underwent Mascular Translocation surgeries.

Macular translocation is a surgical technique designed to move the area of the retina responsible for fine vision (macula) away from the diseased underlying layers (the retinal pigment epithelium and choroid). The macula is moved to an area where these underlying tissues are healthier. Consequently, safe treatment of the sick blood vessels [choroidal neovascularization (CNV)] with, for example, laser treatment can be performed without harming central vision.

For patients who had Macular Translocation surgeries, their normal line of sight are no longer aligned with their macula. Consequently, the Macular Translocation treated eye could show the undesirable "tropia" appearances such as "esotropia" or "exotropia". Further, if patients had their both eyes treated with Macular Translocation surgeries, there could be negative impact to the intended vision function. For example, if the left eye needs to look up to see better, and the right eye needs to look down to see better, then patients can not performance the task because such binocular eye movements are very difficult. This embodiment of redirecting the retinal image location can reduce or correct the "tropia" appearances by relocating the light of sight to the new macular location. This will be even more helpful in the binocular Macular Translocation cases.

In the binocular Macular Translocation cases, this embodiment of the invention could achieve binocular summation, which is at least about 40 percent more effective than monocular vision. Different shift amounts of retinal image locations for the paired eyes are allowed by adjusting the IOL of this embodiment. It takes advantage of the availability of retinal portions with the best neural functions. Neural learning and adaptation restructures the visual pathway and forms image fusion for better vision.

The optics of this embodiment of the present invention to achieve the redirection of images is based on diffractive optics so that the IOL need not be thick and the implantation does not need large incisions. The diffractive optics can be designed as an off centered diffractive single focus and could have an appearance as asymmetric diffractive rings on a centered IOL. In cases that the line of sight is redirected to a new functional area, and the retinal receptors in this area are less in density and large in separations, the diffractive optics of the embodiment of FIGS. 8 and 9 can provide good and suitable optical imagery. Preferably, the retinal imagery provided by this embodiment is no higher than what is suitably resolved by receptors and thus avoids aliasing. Aliasing constitutes false image signals that could provide wrong movement direction to patients.

The embodiments of FIGS. 8 and 9 may be combined with that of the embodiments of FIGS. 2-4 and 6-7 to provide features of each. That is, the lens optics has a diffractive zone structure such as that exemplified in FIGS. 6-7 with appropriate surface modulations to provide an add power of at least 6 diopters and is configured to deflect or redirect images based on diffractive optics in the manner of FIGS. 8 and 9 toward the functional retina to avoid scotoma in the visual field. Thus, an AMD patient can look in the direction of objects to see them without the need to turn away to do so. Further, such an intraocular lens may be implanted in any of the positions shown in FIGS. 2-4 to attain improvement in the ability to see objects when looking in the direction of the object.

Preferably, the diffractive zone structure 24 is made of the same lens material and is of uniform material composition.

To treat patients with AMD, any of the embodiments disclosed may be used in conjunction with administration of an AMD drug to stop and deter further development of AMD. The AMD drug may be an ophthalmic pharmaceutical preparation for the treatment of advanced macular degeneration.

While the foregoing description and drawings represent the preferred embodiments of the present invention, it will be understood that various changes and modifications may be made without departing from the scope of the present invention.

What is claimed is:

1. An intraocular lens comprising, an optic that provides at least two powers of magnification, one being near vision power and another being distance vision power, the optic having a plurality of surface modulations configured to achieve add power indicative of an extent that the near vision focusing power is greater than the distance vision focusing power of the optic, the surface modifications providing the add power to be greater than 6 diopters and having a plurality of zones radially spaced from each other.

2. An intraocular lens comprising, an optic that provides at least two powers of magnification, one being near vision power and another being distance vision power, the optic having a plurality of surface modulations within a diffractive zone structure that are configured to achieve light interference for creating add power indicative of an extent that the near vision focusing power is greater than the distance vision focusing power of the optic, the diffractive zone structure providing the add power to be greater than 6 diopters and having a plurality of diffractive zones radially spaced from each other each with at least one of the plurality of surface modulations, the diffractive zone structure being defined as a function of the add power in accord with $$r_i^2 = (2i+1)\lambda f$$

wherein r$_i$ denotes a radial distance of each of the diffractive zones, i denotes a zone number for which a central zone is denoted by i=0, λ denotes a design wavelength, and f denotes an add power.

3. The lens of claim 2, wherein the optic is either bifocal or multifocal.

4. The lens of claim 2, wherein the surface modulation is a sawtooth configuration.

5. The lens of claim 4, wherein the sawtooth configuration has a step height equal to $$\frac{\lambda}{a(n_2 - n_1)} f_{apodize}$$

wherein

λ denotes the design wavelength

α denotes a parameter that can be adjusted to control diffraction efficiency associated with various orders, n$_2$ denotes the index of refraction of the optic, n$_1$ denotes the refractive index of a medium in which the lens optics is placed, and f$_{apodize}$ represents a scaling function whose value decreases as a function of increasing radial distance from an intersection of an optical axis with an anterior surface of the lens optics.

6. The lens of claim 5, wherein the scaling function f$_{apodize}$ is in accord with $$f_{apodize} = 1 - \left(\frac{r_i}{r_{out}}\right)^3$$

wherein r$_i$ denotes the radial distance of an i$^{th}$ zone, r$_{out}$ denotes an outer radius of a last diffractive zone.

7. The lens of claim 6, wherein a value of the f$_{apodize}$ is one, a value of α is two.

8. The lens of claim 6, wherein the diffraction zone structure is formed to resemble a series of ring configurations of different diameters.

9. The lens of claim 2, wherein the optic is telescopic because of the at least two powers with magnification, further comprising optically aligning the telescopic optic with a non-telescopic optic, the non-telescopic optic lacking multiple powers of magnification.

* * * * *